(12) United States Patent
Goh et al.

(10) Patent No.: US 7,314,749 B2
(45) Date of Patent: Jan. 1, 2008

(54) METHOD AND APPARATUS FOR ASSAY BASED ON LIGHT DIFFRACTION

(75) Inventors: M. Cynthia Goh, Toronto (CA); Richard Loo, Toronto (CA); Jane B. Goh, Toronto (CA); Richard McAloney, Ottawa (CA)

(73) Assignee: Axela Biosensors Inc., Toronto, Ontario (CA)

( * ) Notice: Subject to any disclaimer, the term of this patent is extended or adjusted under 35 U.S.C. 154(b) by 694 days.

(21) Appl. No.: 10/242,778

(22) Filed: Sep. 13, 2002

(65) Prior Publication Data

US 2003/0049693 A1    Mar. 13, 2003

Related U.S. Application Data

(60) Provisional application No. 60/318,624, filed on Sep. 13, 2001.

(51) Int. Cl.
*C12M 1/34* (2006.01)
(52) U.S. Cl. .................. 435/287.1; 422/57; 422/82.05; 422/82.11; 435/287.2; 435/288.7; 435/808; 436/164; 436/165; 436/524; 436/525; 436/527; 436/531; 436/805
(58) Field of Classification Search ...................... None
See application file for complete search history.

(56) References Cited

U.S. PATENT DOCUMENTS 4,436,420 A    3/1984  Depp et al.

4,876,208 A * 10/1989  Gustafson et al. .......... 436/531

(Continued)

FOREIGN PATENT DOCUMENTS

EP    0886141    12/1998

(Continued)

OTHER PUBLICATIONS

International Search Report PCT/ CA 02/01395, (Nov. 11, 2003).

(Continued)

*Primary Examiner*—Christopher L. Chin
(74) *Attorney, Agent, or Firm*—Lynn Schumacher; Nancy Hill; Dowell & Dowell PC

(57) ABSTRACT

The present invention relates to a method and apparatus for detecting analytes in a medium, and more particularly the present invention relates to an assay based on light diffraction which appears or changes upon the binding of analytes to their specific receptors laid out in patterns on a substrate, which has high sensitivity due to the appropriate choice of such patterns. The present invention is based on the principle that the pattern of recognition elements, which gives rise to the diffraction of the incident light in a diffraction-based assay, can be chosen in such a way so as to facilitate detection, and to enhance the signal to be detected compared to known gratings such as parallel straight lines. In one aspect the substrate itself has a surface topography designed to enhance the diffraction pattern signals. In another aspect the substrate is a diffractive optic element having the analyte-specific receptors affixed to the optic element. In another aspect the diffractive optic element is used as a master stamp for producing patterns of analyte-specific receptors which give the signal enhancements.

27 Claims, 7 Drawing Sheets

U.S. PATENT DOCUMENTS

| | | | |
|---|---|---|---|
| 4,882,288 A | * | 11/1989 | North et al. ................ 436/525 |
| 4,992,385 A | * | 2/1991 | Godfrey .................... 436/525 |
| 5,989,923 A | | 11/1999 | Lowe et al. |
| 5,994,150 A | | 11/1999 | Challener et al. |
| 6,180,288 B1 | | 1/2001 | Everhart et al. |
| 6,221,579 B1 | | 4/2001 | Everhart et al. |
| 6,395,558 B1 | * | 5/2002 | Duveneck et al. .......... 436/172 |

FOREIGN PATENT DOCUMENTS

| | | |
|---|---|---|
| EP | 1031828 | 8/2000 |
| WO | 0036416 | 6/2000 |
| WO | 0102839 | 1/2001 |
| WO | 0171322 | 9/2001 |

OTHER PUBLICATIONS

"Diffraction-based assay for detecting multiple analytes", Goh et al., Anal Bioanal Chem (2002) 374: 54-56.

Diffraction-Based Cell Detection Using A Microcontact Printed Antibody Grating; Pamela M. St. John et al., Anal. Chem. 1998, 70, 1108-1111.

Immobilization of antibodies in micropatterns for cell detection by optical diffraction, F. Morhard et al., Elsevier, Sensors and Actuators B 70 (2000) Chemical, 232-242.

* cited by examiner

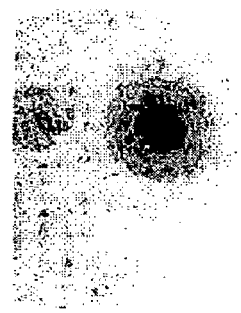
FIG. 4A
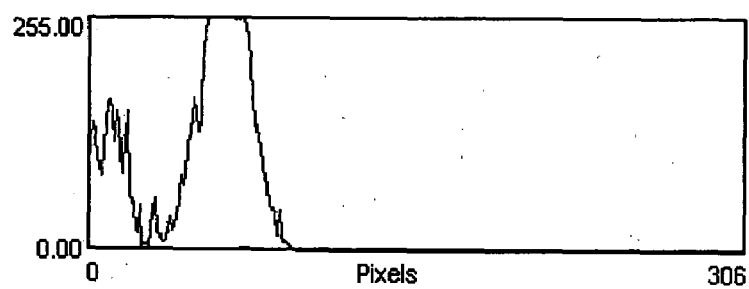
FIG. 4B
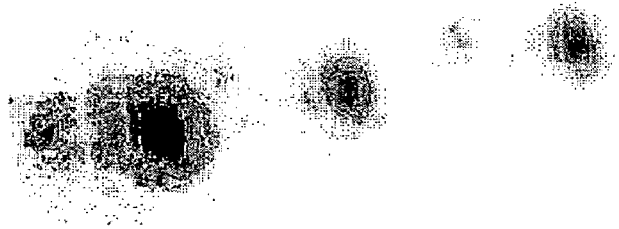
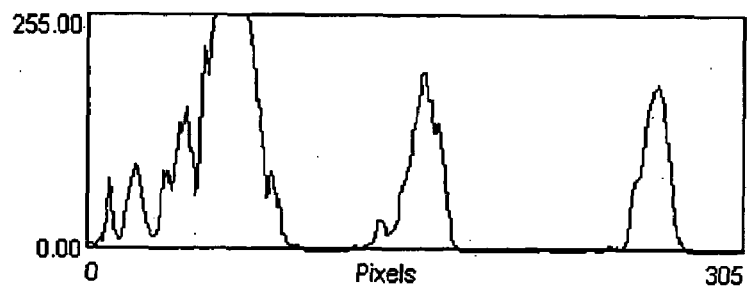

METHOD AND APPARATUS FOR ASSAY BASED ON LIGHT DIFFRACTION

CROSS REFERENCE TO RELATED UNITED STATES PATENT APPLICATION

This patent application relates to United States Provisional patent application Ser. No. 60/318,624 filed on Sep. 13, 2001, entitled METHOD AND APPARATUS FOR ASSAY BASED ON LIGHT DIFFRACTION.

FIELD OF THE INVENTION

The present invention relates to a method and apparatus for detecting analytes in a medium, and more particularly the present invention relates to an assay based on light diffraction which appears or changes upon the binding of analytes to their specific receptors laid out in patterns on a substrate, which has high sensitivity due to the appropriate choice of such patterns.

BACKGROUND OF THE INVENTION

In many instances, it is desirable to determine the presence and the amount of a specific material in solution (the 'medium'). Surface-based assays rely on the interaction of the material to be assayed (the 'analyte') with a surface that results in a detectable change in any measurable property. (For the purpose of this patent, we will define 'analyte' as the material to be assayed; this could be a small molecule, a large molecule such as a protein or DNA, a cell, or a collection of cells, an organism such as a bacterium or virus. 'Analyte-specific receptor, or 'recognition element' will be used to refer to that complementary element that will bind its partner analyte; this could be a molecule or collection of molecules, a biomolecule or collection of biomolecules, such as a protein or DNA, a groove or templated depression on the substrate that has the complementary geometry and/or interaction). In general, in order to assay a specific analyte, the surface is modified so as to offer the appropriate chemical interaction. In immunoassays, for example, one takes advantage of the specificity of the antibody-antigen interaction: A surface can be coated with an antigen in order to assay for the presence of its corresponding antibody in the solution. Similarly, a strand of deoxyribonucleic acid (DNA) can be attached to a substrate and used to detect the presence of its complementary strand in solution. In any of these cases, the occurrence of binding of the analyte to its recognition element on the surface, which thus identifies the presence of the specific analyte in solution, is accompanied by a detectable change. For example, the binding can produce a change in the index of refraction at the interfacial layer; this can be detected by ellipsometry or surface plasmon resonance. Alternatively, the bound analyte molecules may emit light; this emission can be collected and detected, as is the case for fluorescence-based sensors. Non-optical signals may also be used, as in the case of radio immunoassays and acoustic wave sensing devices.

Diffraction is a phenomenon that occurs due to the wave nature of light. When light hits an edge or passes through a small aperture, it is scattered in different directions. But light waves can interfere to add (constructively) and subtract (destructively) from each other, so that if light hits a non-random pattern of obstacles, the subsequent constructive and destructive interference will result in a clear and distinct diffraction pattern. A specific example is that of a diffraction grating, which is of uniformly spaced lines, typically prepared by ruling straight, parallel grooves on a surface. Light incident on such a surface produces a pattern of evenly spaced spots of high light intensity. This is called Bragg scattering, and the distance between spots (or 'Bragg scattering peaks') is a unique function of the diffraction pattern and the wavelength of the light source. There is a unique correspondence between a specific pattern and the pattern of the light that is diffracted by it (the 'diffraction image'), although in practice, diffraction is best illustrated by using periodic patterns, because these yield easily recognized diffraction images of clearly defined regions of high and low light intensity.

Diffraction techniques are commonly used in studies of molecular structure; specifically, X-ray diffraction is used in the identification of chemical compounds and in the determination of protein structures. However, the principle of diffraction, especially in the optical domain, has rarely been invoked for use in assays.

U.S. Pat. No. 4,647,544 (Immunoassay using optical interference detection) describes a light optical apparatus and method, in which a ligand, or an antibody, is arranged in a predetermined pattern, preferably stripes, on a substrate, and the binding between ligand and antiligand, or between an antibody and an antigen, is detected by an optical detector set at the Bragg scattering angle, which is expected to arise due to optical interference. The pattern of ligand or antibody is created by first laying out a uniform layer of antibody on a substrate, then deactivating sections of this coverage.

U.S. Pat. No. 4,876,208 (Diffraction immunoassay apparatus and method) describes the apparatus and reagents for an immunoassay based on a silicon or polysilicon substrate with a pattern of evenly spaced lines of a biological probe (a 'biological diffraction grating') to which binding can take place, The pattern is created by first coating the substrate with an even layer of antibodies, then deactivating regions by the use of a mask and of ultraviolet (UV) lights. This idea is extended to the assay of DNA in U.S. Pat. No. 5,089,387 (DNA probe diffraction assay and reagents), which describes a biological diffraction grating, and a process for its manufacture by first immobilizing a uniform layer of hybridizing agent on a smooth surface, and then exposing this surface to UV radiation through a mask with diffraction grating lines. The UV exposure deactivates the hybridizing agent, leaving a pattern of lines of active hybridizing agents.

In the apparatus described in these two patents, the presence and quantity of analyte is derived from the signal arriving at the detector positioned at one of the Bragg scattering angles. The detection scheme utilizes a photomultiplier tube or photodiode, miscellaneous optics and lock-in amplification that are well-known in the art of detecting small light signals.

U.S. Pat. No. 5,922,550 (Biosensing devices which produce diffraction images) describes a device and method for detecting and quantifying analytes in a medium based on having a predetermined pattern of self-assembling monolayer with receptors on a polymer film coated with metal. The size of the analytes are of the same order as the wavelength of transmitted light, and the diffraction pattern that arises due to binding is strong enough to be visible to the eye. This patent also describes a method of producing the patterned surface by microcontact printing of the self-assembled monolayer of receptors on a metal-coated polymer. This is extended to the case of a predetermined pattern of receptors (not necessarily self-assembling) in U.S. Pat. No. 6,060,256 (Optical Diffraction Biosensor). The technique of microcontact printing of self-assembled monolayers on a metal substrate is described in U.S. Pat. No. 5,512,131 (Formation of microstamped patterns on surfaces and derivative articles).

Microcontact printing is a technique of forming patterns of micrometer dimensions on a surface using an elastomeric stamp; the material to be patterned serves as the "ink" and is transferred by contacting the stamp to the surface. Microcontact printing of proteins on silicon, silicon dioxide, polystyrene, glass and silanized glass is reported in Bernard, A; Delamarche, E.; Schmid, H.; Michel, B.; Bosshard, H. R.; Biebuyck, H.; "Printing Patterns Of Proteins" Langmuir (1998), 14, 2225-2229.

To utilize diffraction techniques in surface-based assays, it is important to be able to produce a material patterned with receptors, and the five patents discussed above have outlined their ways of doing so. In addition, other techniques that exist in the literature may be adaptable for patterning. For example, using photolithographic techniques, oligonucleotides have been immobilized on a substrate in arrays such that each array is a distinct species. U.S. Pat. Nos. 5,831,070 and 5,599,695 show how this is done through the use of deprotection agents in the gas phase. This approach has not been used in the creation of patterns for diffraction assays, but can be adapted for such with the design of an appropriate mask.

To summarize the prior art, it has been shown that diffraction of light that occurs upon binding of an analyte to its partner receptor that has been patterned on a substrate can be used for an assay. In U.S. Pat. Nos. 4,647,544 and 4,876,208, the pattern of evenly spaced lines (grating) is used, and the signal is detected by a detector at the expected location of the Bragg peaks. The diffraction intensity is low enough and necessitates the use of a lock-in amplifier and associated optics and electronics for its detection. In U.S. Pat. Nos. 5,922,550 and 6,060,256, the analyte being assayed is large enough, so that the diffraction pattern is visible to the eye. The pattern on the surface consists of simple geometric elements such as circles of uniform size, and which are evenly spaced.

These patents which make up the prior art do not consider the importance of the type of pattern on the surface, upon which this invention is based. The present invention specifically refers to assays using the principles of diffraction wherein the surface pattern is different from the prior art of evenly spaced lines (a grating), or evenly spaced circles. The choice of design for the surface pattern can enhance the effectiveness of the assay, for example, by enhancing the signal.

SUMMARY OF THE INVENTION

An objective of the present invention is to provide a method for the assay of analytes using the principles of light diffraction from a patterned surface, the sensitivity of which assay is enhanced by appropriate choice of the pattern on the surface. In accordance with this objective the present invention provides a method for detecting analytes in a medium, the article for enabling such detection, the process for producing such article, and the apparatus for carrying out the assay.

The article of this invention is a substrate upon which is laid out patterns of recognition elements or analyte-specific receptors. The patterns are chosen in such a way as to have large diffracted signal intensity at desirable locations, such as away from regions of high noise like that emanating from scattering of the main beam.

The method of this invention involves exposure of the said patterned substrate to a medium containing the analyte complementary to the patterned recognition element for a period of time to allow for binding to take place. The binding event between analyte and its partner is accompanied by either a change in the local thickness of the layer on the substrate or in the local index of refraction, or both, resulting in the alteration of the optical properties at the interface between the substrate and medium. But because the probe molecules are laid out in a predetermined pattern, light incident on the substrate is not scattered uniformly, but is rather diffracted. The binding event will be indicated by the appearance or alteration of a specific diffraction image. In one embodiment of this invention, the intensity of diffracted light is measured to enable a quantitative assay.

Extensions to the case of multiple analytes can be effected by laying down multiple patterns within a selected region such that at least parts of each pattern is simultaneously exposed to the incident illumination. Furthermore, each type of recognition element is laid out in a unique pattern, distinct from the pattern of every other type of recognition element. There is a correspondence between the pattern of the diffracted light and the pattern on the substrate, and observation of the pattern of diffracted light (the 'diffraction image') can be used for the identification of the analytes present in the original medium. Alternatively, different recognition elements may be laid out in different areas of the substrate either in the same or in different patterns; in this case, each region is assayed independently by independent exposure to the incident illumination. In the case of multiple patterns of multiple recognition elements, it is desirable to have regions of high intensity such that at least one region is distinct to each pattern employed. In other words the diffraction patterns may overlap but each pattern should have at least one unique spot.

The apparatus for implementing the method includes a light source, a means of supporting the patterned substrate, and a light detector positioned to collect the diffracted light, and connected to appropriate data collecting devices.

In one aspect of the invention there is provided a sensing element for use in a light diffraction assay for detecting the presence or absence of at least one analyte, comprising:

a substrate including a planar surface and analyte-specific recognition binding element means laid out on said planar surface in a pre-selected pattern such that when analytes are present in an assay they bind to said analyte-specific recognition element means, said pre-selected pattern being selected so that under illumination by a beam of light a pattern of at least one diffraction spot is produced, said at least one diffraction spot being located in a pre-selected position relative to said beam of light, said pre-selected pattern excluding said analyte-specific recognition element means arrayed in parallel straight lines of substantially equal width spaced evenly from each other, or in a periodic array of circles.

The present invention also provides a sensing element for use in a light diffraction assay for detecting the presence or absence of at least one analyte, comprising:

a substrate including a planar surface and analyte-specific recognition binding element means laid out on said planar surface in a pre-selected pattern such that when analytes are present in an assay they bind to said analyte-specific recognition element means, said pre-selected pattern being selected so that under illumination by a beam of light a diffraction pattern is produced having at least one diffraction spot spaced from said beam of light and having a sufficient amount of the intensity of said diffraction pattern being located at said at least one diffraction spot to indicate presence of analytes bound to said analyte specific receptors.

The present invention also provides a sensing element for use in a light diffraction assay for detecting the presence or absence of at least one analyte, comprising:

a substrate having analyte-specific receptors bound to a surface of said substrate for binding selected analytes, said surface of said substrate having a surface topography which, upon illumination by a beam of light and with analytes bound to said analyte-specific receptors, gives rise to a sufficient number of diffraction spots in pre-selected positions spaced from said beam of light indicative of the presence of analytes bound to said analyte-specific receptors.

The present invention also provides a sensing element for use in a light diffraction assay for detecting the presence or absence of at least one analyte, comprising:

a diffractive optic element having analyte-specific receptors bound to a surface of said diffractive optic element for binding selected analytes.

The present invention provides a diffraction binding assay method for detecting analytes in a medium, comprising:

providing a substrate having selected analyte-specific receptors bound to a surface of said substrate, said surface of said substrate having a surface topography which, upon illumination by a beam of light and with analytes bound to said analyte-specific receptors, gives rise to a pre-selected number of diffraction spots in pre-selected positions spaced from said beam of light indicative of the presence of analytes bound to said analyte-specific receptors;

contacting said surface of the substrate with the medium for a sufficient time to permit preselected analytes present in solution to bind with their analyte-specific receptors; and illuminating said substrate with a beam of light and detecting light diffracted from said substrate surface and analysing said diffracted light for presence of diffraction spots representative of binding of said analyte to said analyte-specific receptors on said surface.

There is also provided a diffraction binding assay method for detecting analytes in a medium, comprising:

providing a diffractive optic element and coating analyte-specific receptors bound to a surface of said diffractive optic element for binding selected analytes;

contacting said surface of said diffractive optic element with the medium for a sufficient time to permit preselected analytes present in solution to bind with their analyte-specific receptors; and illuminating said diffractive optic element with a beam of light and detecting light diffracted from said diffractive optic element and analysing said diffracted light for presence of diffraction spots of sufficient intensity representative of binding of said analyte to said analyte-specific receptors on said diffractive optic element.

The present invention provides a diffraction binding assay method for detecting analytes in a medium, comprising:

providing a substrate including a planar surface and analyte-specific recognition binding element means laid out on said planar surface in a preselected pattern such that when analytes are present in an assay they bind to said analyte-specific recognition element means, said pre-selected pattern being selected so that illumination of said pre-selected pattern by a beam of light and with analytes bound to said analyte-specific receptors gives rise to a sufficient number of diffraction spots in pre-selected positions spaced from said beam of light indicative of the presence of analytes bound to said analyte-specific receptors;

contacting said planar surface of the substrate with the medium for a sufficient time to permit preselected analytes present in solution to bind with their analyte-specific receptors; and illuminating said substrate with a beam of light and detecting light diffracted from said substrate surface and analysing said diffracted light for presence of diffraction spots representative of binding of said analyte to said analyte-specific receptors on said planar surface.

There is also provided an apparatus for detection of analytes in a medium using diffraction of light, comprising:

a source of illumination;

a sensing element including a substrate having a planar surface and analyte-specific recognition binding element means laid out on said planar surface in a pre-selected pattern such that when analytes are present in a medium they bind to said analyte-specific recognition element means, said preselected pattern being selected so that under illumination by a beam of light a diffraction pattern is produced having at least one diffraction spot spaced from said beam of light with a substantial portion of the intensity of said diffraction pattern being located at said at least one diffraction spot, said source of illumination being positioned so as to illuminate said substrate surface;

detection means positioned with respect to said sensing element to detect light diffracted from said illuminated surface; and processing means for analysing said diffracted light for presence of a diffraction pattern representative of binding of one or more analytes with their analyte-specific receptors and identifying from said diffraction pattern one or more analytes present in said medium.

Also provided is an apparatus for detection of analytes in a medium using diffraction of light, comprising:

a source of illumination;

a sensing element including a diffractive optic element having analyte-specific receptors bound to a surface of said diffractive optic element for binding selected analytes, said source of illumination being positioned so as to illuminate said diffractive optic element;

detection means positioned with respect to said sensing element to detect light diffracted from said diffractive optic element; and processing means for analysing said diffracted light for presence of a diffraction image representative of binding of one or more analytes with their analyte-specific receptors and identifying from said diffraction pattern analytes present in said medium.

The present invention also provides an apparatus for detection of analytes in a medium using diffraction of light, comprising:

a source of illumination;

a sensing element including a substrate having analyte-specific receptors bound to a surface of said substrate for binding selected analytes, said surface of said substrate having a surface topography which, upon illumination by a beam of light and with analytes bound to said analyte-specific receptors, gives rise to a pre-selected number of diffraction spots in pre-selected positions spaced from said beam of light indicative of the presence of analytes bound to said analyte-specific receptors, said source of illumination being positioned so as to illuminate said substrate surface;

detection means positioned with respect to said sensing element to detect light diffracted from said illuminated surface; and processing means for analysing said diffracted light for presence of a diffraction image representative of binding of one or more analytes with their analyte-specific receptors and identifying from said diffraction pattern analytes present in said medium.

BRIEF DESCRIPTION OF THE DRAWINGS

The invention will now be described, by way of example only, reference being had to the accompanying drawings, in which;

FIG. 2b is the corresponding diffraction pattern obtained when analytes bind to analyte-specific receptors coated on the sinusoidal surface of FIG. 2a;

FIGS. 4a and 4b are the diffraction images obtained upon binding to the patterned antibodies in FIGS. 3a and 3b, respectively, the scales are the same on both FIGS. 4a and 4b;

DETAILED DESCRIPTION OF THE INVENTION

The present invention provides a method for the assay of analytes using the principles of light diffraction from a patterned substrate. As mentioned in the background, the prior art has shown the feasibility of using the diffraction of incident light to indicate the presence of a specific type of analyte. The present invention provides a diffraction-based assay that is capable of high sensitivity by utilizing patterns on the substrate that are chosen to enhance the diffraction signal relative to those normally achieved with diffraction patterns using evenly-spaced parallel lines, which constitutes diffraction gratings.

In order to carry out an assay based on diffraction, recognition elements are laid out on a substrate to define a pattern. In a preferred form, this patterned substrate is non-diffracting. The binding of analytes complementary to these recognition elements will alter the local index of refraction and/or topography such that, upon illumination, the incident light is diffracted. Detection of such diffracted light indicates the occurrence of a binding event between analyte and receptor, and hence the presence of the analyte in the original medium being assayed. In another embodiment, the initial substrate itself diffracts light. In this case, the binding event will still alter the local index of refraction and/or topography, and the intensity of the diffracted signal will change. For ease of signal detection, a preferred apparatus for this case is one that involves filtering such that this initial signal is nulled, using either optics or using software.

Figure 1:
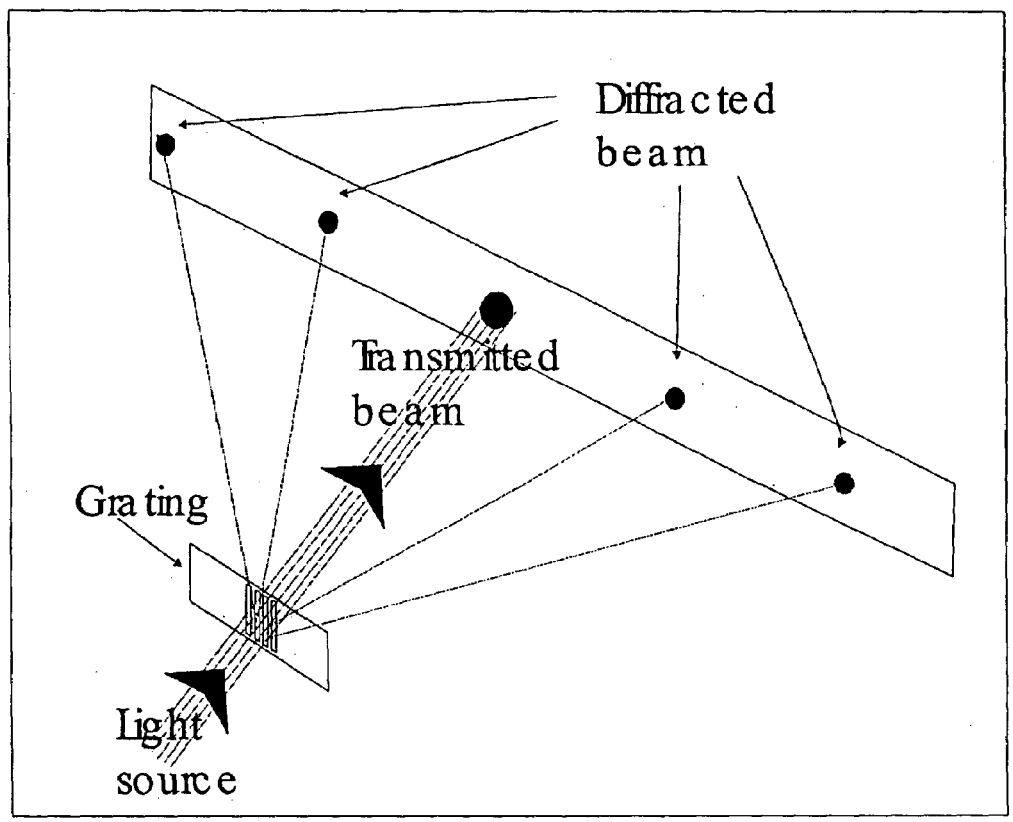
FIG. 1 is a schematic of a typical grating showing the corresponding diffraction pattern arising from such a grating.

It is well known in the field of optics that there is a correspondence between a given pattern and the pattern of light that is diffracted from it. This principle has not been utilized to the fullest in assays, and is the subject of the present invention. The most common pattern used in diffraction studies is that of evenly spaced lines (a 'grating'), shown in FIG. 1, and U.S. Pat. Nos. 4,647,544 and 4,876,208 are based on such. The diffraction pattern that arises from a grating is a series of evenly spaced bright dots ('Bragg peaks') with diminishing light intensity as one moves away from the central beam of light. The spacing of the Bragg peaks is determined by the spacing of the lines in the grating. In any assay, it is important to maximize the signal-to-noise ratio in order to increase sensitivity. In a diffraction-based assay using the example of the grating shown in FIG. 1, there typically is noise due to scattering of the main beam, which can be large compared with the diffracted signal because of the high intensity of the main beam which can swamp or wash out the typically small changes brought about by the binding events. One can try to reduce the noise from the main beam and from stray scattering by detecting the diffracted signal as far away from the main beam as possible; however, the diffracted signal also rapidly diminishes far from the main beam as mentioned above. Thus the sensitivity and applicability of diffraction-based assays using a grating such as shown in FIG. 1 is limited.

The present invention provides methods and devices for enhancing signals obtained in a diffraction-based assay, together with the ability to manipulate chemistry at a surface. The main concept is based on the principle that the pattern of recognition elements, which gives rise to the diffraction of the incident light in a diffraction-based assay, can be chosen in such a way so as to facilitate detection, and to enhance the signal to be detected. The pattern of receptor molecules on the substrate may thus be made quite complex in order to enhance signal and simplify detection. The detailed requirements may vary depending on the specific application and constraints. There are three different methodologies and sensing elements that are disclosed herein to achieve this result.

i) Sensing Element Substrate With Selected Surface Topography

Figure 2A:
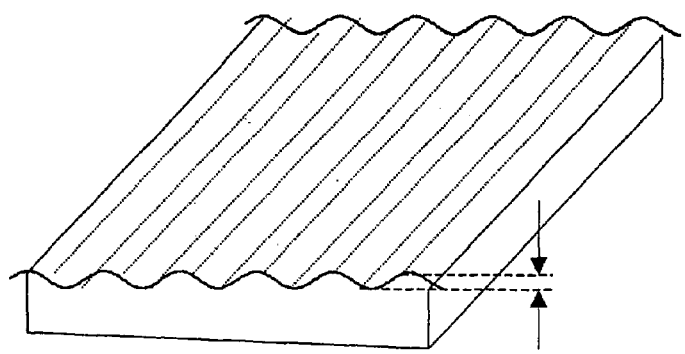
FIG. 2a is a schematic of sensing element having a sinusoidal surface.
Figure 2B:
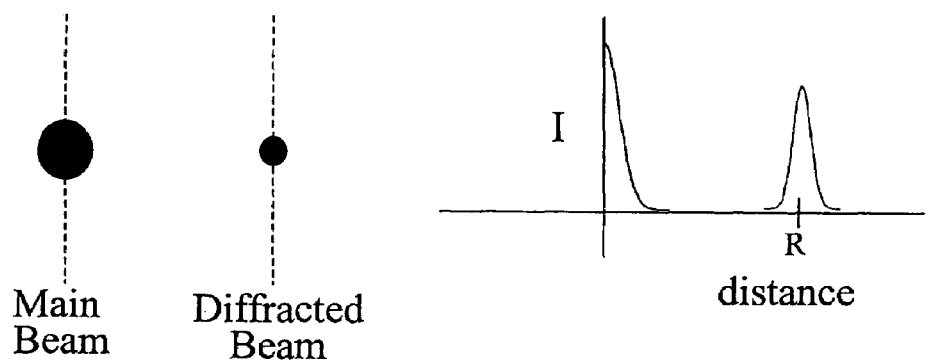
Figure 2C:
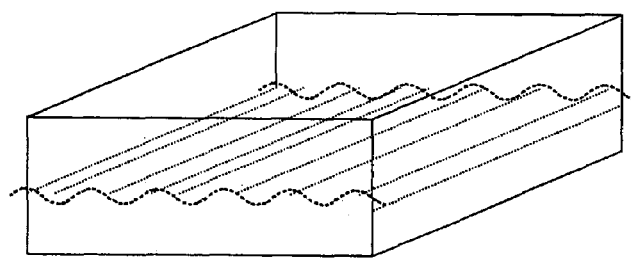
FIG. 2c shows the rippled surface covered with analyte-specific receptors in contact with a medium of matching refractive index; so that the interface is essentially invisible, when binding of analyte to analyte-specific receptor occurs, there is a change of refractive index at the interface, which causes it to diffract light.

One embodiment of the present invention comprises a substrate to which the pattern recognition elements are bound which has a surface topography selected to give a diffraction image characterized by one or more diffraction spots spaced from the main light beam which are more intense than the spots obtained using standard diffraction gratings. One example is a pattern that gives rise to only one diffracted spot, so that most of the diffracted intensity is localized at this spot, and which is located as far away from the incident beam as possible, so that scattering due to the main beam is minimized. A surface having a sinusoidal function sin(kx) (or cosine(kx)) as shown in FIG. 2a will yield exactly one element in the Fourier transformation, located at +k as shown in FIG. 2b. To make k as large as possible (that is, the diffracted light be as far removed from the incident beam), the period of the sine or cosine should be about half the wavelength of the illumination. The analyte-specific receptors cover the whole substrate so that the patterned recognition element is a composite of the rippled substrate plus the analyte-specific receptors covering the surface. The assay is preferably performed in contact with a solution the refractive index of which matches closely that of the patterned substrate, such that the interface is essentially invisible, and none or very little light is diffracted prior to binding. In other words the reason index matching is preferred with this type of substrate is that the large signal a topography can generate will overwhelm the change due to binding. In the case of a flat surface, there is no such signal diffraction signal present so index matching is not required and one can use total internal reflection.

The binding event highlights the rippled substrate by destroying the index matching, and gives rise to the lone diffraction spot, see FIG. 2b. It will be understood that the use of cosine (sine) surface topographies are only illustrative and a topography other than sinusoidal may be preferable.

For example, a topographical grating comprising evenly spaced lines but which have larger topography than the analyte receptors can be used and the analyte receptors are immobilized to cover the entire substrate, is one possibility. The substrate with the topographical grating and the medium are index matched initially, so that no diffraction is observed. The binding of analytes in the medium with the analyte specific receptors breaks the index matching, thus highlighting the grating, and resulting in a diffraction signal.

While the above examples illustrate sensor substrates having surface topographical features that are much larger in scale than the analyte specific receptors, it will be understood that the sensor elements may be constructed with molecular scale topographical features, for example the sensor element could include templated grooves the size of a large molecule having a complementary geometry and interaction to the analytes. In other words, the analyte specific receptors may comprise molecular to microscopic size indentations that would provide complementary shape and interaction to specific proteins or cells, which are the analytes being tested for.

ii) Patterned Flat Substrates

The sensing element for the assay may be a solid substrate having laid out on its planar surface a set of recognition elements or analyte-specific receptors in a pattern, either directly or through an intervening layer. The pattern is chosen to satisfy whatever criteria are desired for a specific assay, be it the enhancement of resolution, or simply for artistic purposes. In an assay for multiple analytes on the same region, it may be desirable to choose surface patterns for each analyte that will give rise to as different a diffraction image as possible, or at least contain regions of high diffracted signal intensity that do not overlap with those for other analytes. In other words the entire diffraction image may not necessarily need to be distinct for each analyte. All that is needed is that there is one region or spot of each analyte that is distinct from others (i.e. well-separated spatially). In one embodiment of this invention, the pattern of receptors on the substrate is chosen in such a way as to enhance the intensity of the diffracted signal away from the main beam, and reduce the intensity at the main beam as much as possible. The diffracted signal is preferably concentrated in as few locations as possible.

iii) Diffractive Optic Elements

Another class of pattern of interest is that corresponding to optical elements that steer light using the principles of diffraction, typically resulting in predetermined distinct patterns (diffractive optical elements). Most optical elements manipulate light using the principles of reflection or refraction. Diffractive optic elements manipulate light by using the principles of diffraction: portions of the wavefront are retarded selectively using patterns on a substrate typically glass, but other materials may be used as well. Diffraction permits a more versatile and powerful means of steering light. The patterns may be surface patterns formed on the surface of the element, or bulk patterns formed through the bulk of the material. Diffractive optic elements may have quite complicated patterns, but their versatility in manipulating light is useful in the current objective of optimizing properties of the diffraction image; a complicated pattern on the substrate is thus preferred compared with the prior art patterns of evenly spaced lines or circles.

Diffractive optic elements are commercially available, or can be manufactured to specifications, and common examples are attachments to laser pointers that produce patterns such as a French cross, star, circles and the like. In this invention we are interested in diffractive optical elements that diffract light because of their surface topographical pattern. This type of diffractive optical element is useful in this invention in either of two ways: (1) the probe molecules are immobilized to cover the whole surface of the element, which is then brought into contact with the medium to be assayed as described in (i) above. The refractive index of the medium is preferably matched or close to that of the optical element; (2) The diffractive optical element is used as a master for microcontact printing such that an elastomeric stamp is made from its surface topography. The probe molecule is thus patterned onto a substrate using this elastomeric stamp according to the principles of microcontact printing and the substrate is utilized as in (ii) above.

When being used, since the diffractive optic itself will have a large diffraction signal itself unless the medium is index matched so it is a difference or change in intensity that is monitored once the element is immersed in the medium. Intensity measurements may be made before exposure to the medium containing the analytes in order to get a baseline or calibration which may be stored in the processor. The presence of diffraction spots representative of binding of the analyte to the analyte-specific receptors is indicated by a change in intensity of the measured diffraction signal.

A specific type of substrate that may be used in the diffraction-based assay of the present invention is a diffractive optic beam splitter, which is an element that produces a preset number of beams of approximately equal intensities from one incident beam. If this type of pattern is employed in a diffraction-based assay, the binding event will give rise to a comparatively large diffracted signal, which is desirable in detection enhancement.

Complex patterns on a flat surface may be created by a variety of means. Photolithography can be employed in many ways: light can be used to initiate a reaction to activate or deactivate surface species, and by the appropriate application of masks, patterns can be formed. Printing techniques, such as microcontact printing, inkjet printing and robotic spotting enables the deposition of material in desired patterns. The deposited material is either held to the substrate by physical adsorption, or can be covalently bound to the surface or a surface layer deposited on the substrate for the specific purpose of binding to the pattern recognition species.

For example, in addition to using a diffractive optic element itself as a substrate for recognition elements, a highly preferred patterned substrate may be prepared by microcontact printing using a diffractive optic element as a master and transferring the pattern from the diffractive optic element to a smooth flat substrate surface, such as for example glass, polymer, ceramic, semiconductor or metal, with or without additional coatings. Diffractive optic elements have topographical patterns that are much more complicated than a grating of evenly spaced lines. However, they can easily be used as a mold to form an elastomeric stamp for use in microcontact printing. The pattern printed in this manner will not be an exact replica of the diffractive optic element since only the spacing between topographic features will be reproduced, but not the depth of the grooves. However, the diffraction signal will be much enhanced over that produced by an ordinary grating comprising straight parallel grating lines.

The assay is performed by contacting the patterned substrate with the analyte-containing medium. The solid substrate upon which the pattern of recognition elements is laid may be transparent, partially transparent, or reflecting at the wavelength of the incident illumination. In the case of a transparent substrate, analyte-specific receptors may be patterned on one or both surfaces of the substrate. Once the recognition element that is capable of specific binding (e.g., protein, oligonucleotide, antibody, etc.) is laid out on the surface in a preselected pattern, the medium to be assayed is contacted with the substrate, allowing analytes present in the medium to bind to their complementary recognition element.

When a particular analyte is present in the medium, the subsequent binding event between analyte and its complementary recognition element is accompanied by a change in the local thickness of the layer on the substrate and/or in the local index of refraction. Both the change in thickness and the change in index of refraction will alter the optical properties at the interface between the substrate and medium in regions where the binding has taken place. Since the recognition elements are present on the substrate in a predetermined pattern, light incident on the substrate will not be scattered uniformly, but rather will be diffracted. In one embodiment of this invention, the patterned substrate is non-diffracting, and the binding events result in an observable diffraction image. In another embodiment, the patterned substrate itself produces an observable diffraction image, but the binding events alter the intensities of the diffracted signal.

The diffracted signal strength may be enhanced by the addition of one or more secondary species selected to localize on the already immobilized analytes. The secondary species may contain a substance that will enhance the change in index of refraction (such as a chromophore, a metal colloid with a plasmon band, resonant with the source wavelength, or an enzyme that can cause a precipitate to form when appropriate reagents are added), or enhance the change in height above the substrate (such as a large particle, a metal colloid, a polymer colloid, a quantum dot, a protein), or both.

Alternatively, the analytes may be pre-treated so as to be first coupled to a material that will enhance the signal obtained upon binding, either through a change in refractive index, or in height, or both. This material may be a polymer colloid, a large molecule, a chromophore or a metal colloid. The chromophore or metal colloid should preferably absorb radiation at the wavelength of the source illumination.

In one embodiment of the invention, after the substrate surface has been exposed to the medium being screened for the analytes, the substrate is rinsed and dried prior to the diffraction measurement. In another embodiment, the assay is performed in situ with the substrate immersed in the solution containing the analyte. This is the preferred mode when index matching is desired to enhance the diffraction signals as discussed above with respect to the substrates with the modified surface topography. In this case, the kinetics of the binding event may be examined by monitoring the evolution of the diffraction signal. The assay is made quantitative by a measurement of the intensities at selected regions of the diffraction signal, and by the use of predetermined calibration standards or alternatively by fitting to known binding kinetics.

The assay has been described for a single type of analyte. The present method includes extension to detecting multiple analytes in a medium and involves producing multiple patterns of recognition elements within the same substrate. The pattern for each type of recognition element may either be distinct from that of others, or they may be the same, but simply located in different regions of the substrate. The following are non-limiting examples of simple distinct patterns: (1) They may consist of different geometric elements (lines, circles, etc.) (2) They may be of the same geometric elements but arranged with different periodicities. (3) They may be of the same geometric elements with the same periodicity but rotated with respect to each other, provided the patterns do not have rotational symmetry. (4) They may be a mixture of any of the above. In the case of multiple patterns of multiple recognition elements, it is desirable to have regions of high intensity such that at least one region is distinct to each pattern employed. In other words the diffraction patterns may overlap but at each pattern should have at least one unique spot.

In applications in which moisture may be problematic, the substrate may be placed in a cell that is partially evacuated in order to reduce moisture. This is advantageous where it is desirable to reduce the signal strength that may arise due to water condensation. However, in the case where the analytes but not their partner receptors are favoured by water, the presence of water condensation (also called 'condensation figures') can be utilized to enhance the diffraction signal.

Figure 6C:
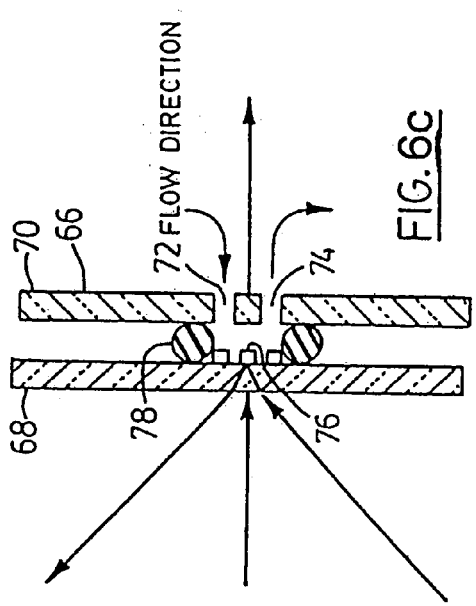
FIG. 6c is a perspective view of an alternative embodiment of a flow cell constructed in accordance with the present invention.
Figure 6D:
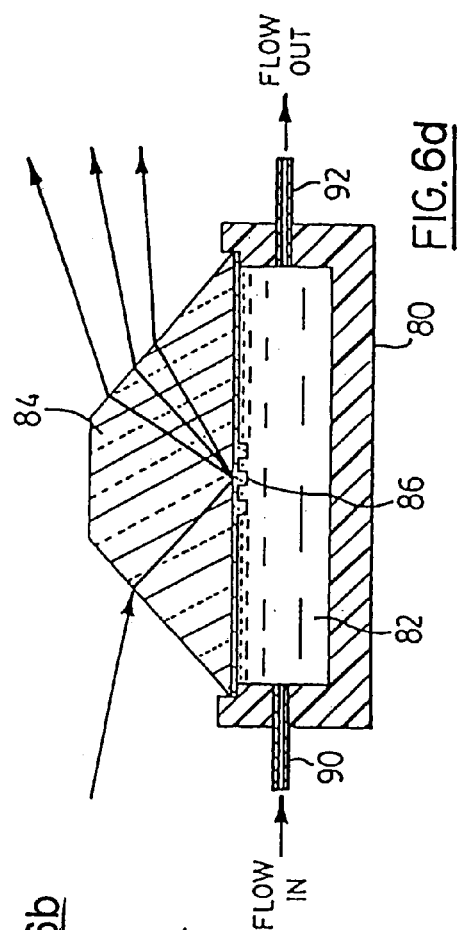
FIG. 6d is a cross-sectional view of a flow cell using total internal reflection.
Figure 6A:
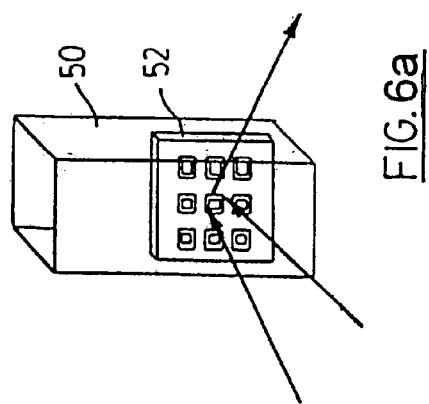
FIG. 6a is a perspective view of a cell for performing an assay in the static mode.

In another embodiment of the invention, the assay may also be performed in situ by placing the substrate into a chamber into which the medium can be introduced. FIG. 6*a* shows a cell 50 with a substrate 52 immersed in a liquid being tested for the presence of one or more of the analytes in a static configuration with no flow-through. Analyte-specific receptors are patterned on one or both surfaces of substrate 52.

Figure 6B:
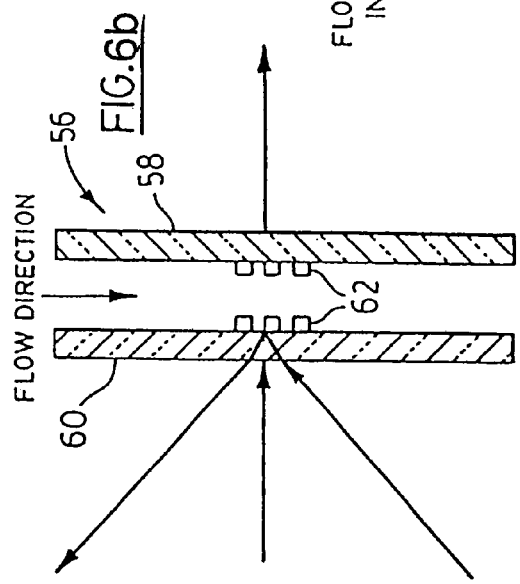
FIG. 6b is a cross-sectional view showing an embodiment of a flow cell constructed for performing the present assay.

FIG. 6*b* shows a flow configuration comprising a cell 56 comprising spaced parallel walls 58 and 60 with analyte-specific receptor patterns formed on the insides of each of the walls. The liquid is continuously flowed through the cell during operation and the reflection or transmission mode may be used as indicated by the arrows. FIG. 6*c* shows another embodiment of a flow cell 66 comprising spaced parallel walls 68 and 70 with wall 70 having an inlet port 72 and an outlet port 74. The analyte specific receptor pattern 76 is formed on the inner surface of wall 68 and an O-ring 78 is used to seal the flow chamber. In each of these embodiments the chamber should have at least one window transparent to the incident illumination. The substrate within the chamber is located in direct line of illumination, and the assay is performed either in reflection or transmission, as described previously. In another embodiment, the fluid chamber may comprise the patterned substrate as one or more of its windows. In these embodiments, the time dependence of the binding events may be monitored simultaneously for all analytes. This may be useful for measurement of relative binding affinities.

In certain cases, as will be described in the examples hereinafter, the diffracted signal will be strong enough to be visible to the unaided eye under proper lighting conditions. In this case, all that is needed is the observer's eye, or for a more permanent record, any camera, or similar imaging device. For quantification of low intensity signals, a sensitive CCD array detector or a PMT may be used. For further signal enhancement, lock-in detection as well as amplification schemes known to those skilled in the art may be employed. As discussed previously, the image, or a part thereof, obtained as an electronic signal from the detector is stored on a computer and image analysis software is then used to identify the patterns on the substrate that gave rise to the observed diffraction image thus identifying which analytes are present in the medium. A code may be written on the substrate itself that identifies which analyte-specific receptors are present. The presence of signals at specific locations relative to a standard encoded location within the diffraction image corresponds to the presence of specific analytes. Quantification of signals at defined locations enables quantification of the amount of different analytes.

In operation, the recognition elements that are capable of specific binding (e.g., protein, oligonucleotide, antibody, etc.) are laid out on a surface in preselected patterns. The medium to be assayed is contacted with the substrate, allowing analytes present in the medium to bind to their complementary recognition element. It should be noted that the recognition element could be a structural or topographical feature such as grooves formed in the top surface of the substrate having dimensions and/or interactions to trap the target of interest such as a bacterium. In one embodiment of this invention, the substrate is rinsed and dried, and placed in one of the devices previously described such that the substrate with the bound analytes is placed in direct line of the light beam from the light source 32. The substrate may be a dipstick.

While it is simplest to utilize a clear medium, such as an aqueous solution, this method can also be used for assay of analytes present in other media. The medium may generally be a fluid including gas or liquid and the analytes can include various biological pathogens, environmental toxins or chemical warfare agents dispersed in air. In one embodiment of this invention, analytes present in complex media such as urine, blood, serum, plasma or other turbid media are assayed. If the medium is not completely transparent to the incident illumination, the assay is best performed under reflection configuration. The assay of analytes in complex media may be complicated by degradation of signal-to-noise due to scattering and/or absorption of the incident illumination by the medium. Thus, in one embodiment of the invention the apparatus used to perform the assay uses total internal reflection of the incident light from the substrate-medium interface. Referring to FIG. 6d, a substrate 84 having analyte-specific receptor patterns 86 is in contact on one side thereof with the medium 82 being tested, which is contained within a chamber 80. Light is totally reflected from the interface between substrate 84 and medium 82. The cell operates as a flow cell when fluid is pumped through tube 90 into chamber 80 and out of tube 92. In another embodiment of this invention, the incident illumination is chosen so that the complex medium is transparent at the wavelength of the light, for example, the use of near-infrared laser wavelengths for the assay of fluids such as blood and the like.

Figure 5A:
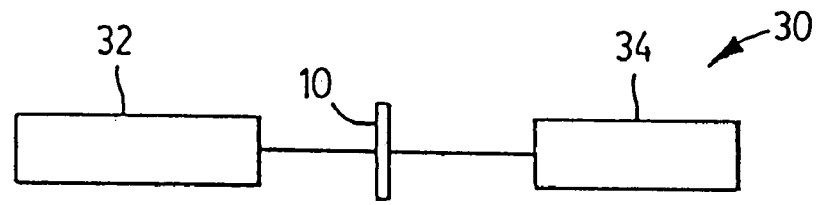
FIG. 5a shows a diagrammatic illustration of an apparatus for performing an assay in accordance with the present invention using a transmission configuration.
Figure 5B:
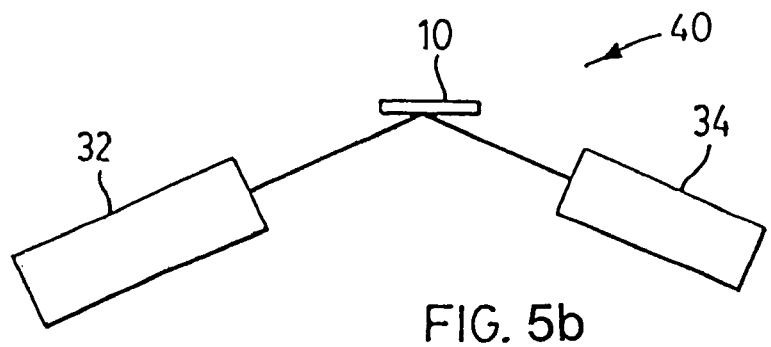
FIG. 5b shows a diagrammatic illustration of an apparatus for performing an assay using a reflection configuration.
Figure 5C:
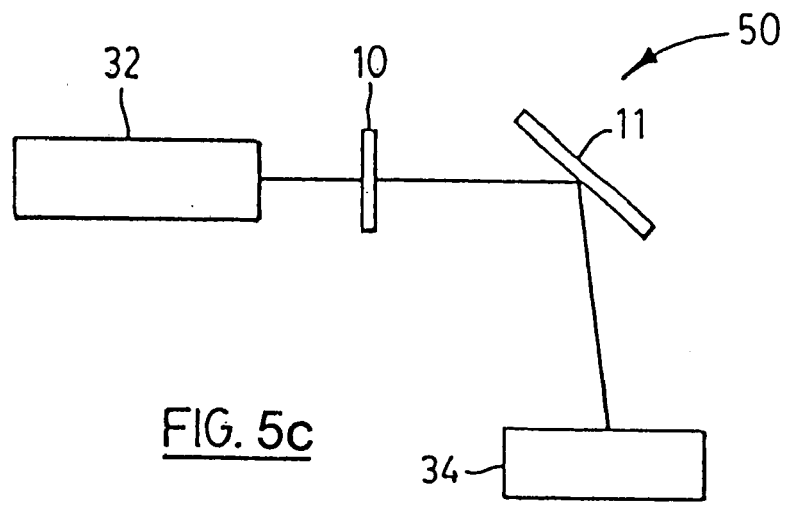
FIG. 5c shows a diagrammatic illustration of an apparatus for performing an assay in accordance with the present invention where a mirror is mounted on a rotation stage to direct light from the substrate to the detector.

Referring to FIGS. 5a, 5b and 5c, detector 34 must be sensitive to the illumination of choice. The detector 34 may be a position sensitive photodiode, a photomultiplier tube (PMT), a photodiode (PD), an avalanche photodiode (APD), a charged-coupled device (CCD) or a CMOS array, the unaided eye, a camera, a photographic plate, or any other imaging device. In one embodiment of this invention, the transmitted or reflected signal is collected by an imaging optical fibre and directed to an imaging detector. Detector 34 is attached to the appropriate accessories to provide power and enable signal collection and data processing. If a position sensitive photodiode is used it is first calibrated; the intensity of the signal reflects the position of the pattern impinging on the detector.

The photodiode, photomultiplier tube or avalanche photodiode is mounted on a translation stage. By moving the detector on the stage, the pattern of high and low light levels are mapped out. Alternatively, the PMT or (APD) may be held in a stationary position. A mirror is positioned to direct the light from the substrate to the PMT, PD or APD. This mirror is mounted on a rotation stage, and by rotating the stage, the pattern of low and high light levels can be mapped out on the PMT, PD or APD as shown in FIG. 5c.

When a CCD array or other imaging device is used, it is positioned to collect either the full diffraction image, or a part thereof. In the latter case, the imaging device is mounted on a translation stage to enable inspection of selected regions of the diffraction image; changes in the intensities signify the binding event(s). The following non-limiting examples are intended to further illustrate the invention.

EXAMPLE 1

Preparation of Patterned Substrate By Microcontact Printing

The substrates were patterned by microcontact printing essentialy following the procedure described in Bernard, A; Delamarche, E.; Schmid, H.; Michel, B.; Bosshard, H. R.; Biebuyck, H.; "Printing Patterns Of Proteins" Langmuir (1998), 14, 2225-2229. For evenly-spaced masters (diffraction grating), electron microscope grids or masters prepared by standard photolithography were used; otherwise various diffractive optics (Thor Labs) were employed. The poly (dimethylsiloxane) (PDMS) stamps were fabricated by using typically 10% crosslinking (Sylgard 184 Silicone elastomer kit, Dow Corning Corporation purchased from Paisley Products, Ontario Canada) and curing at 50-60° C. for 14-18 h. The PDMS stamps prepared in this manner have a diffractive surface of ~50 mm². The PDMS stamp was cleaned by sonication in a 2:1 solution of distilled and deionized water (ddH$_2$O)/ethanol for 5-10 min, followed by drying under a stream of nitrogen gas (N$_2$) and applying a fresh piece of adhesive tape to the stamp surface. The tape was removed from the stamp surface after a few minutes, 150-200 µL of protein at 50-100 µg/mL in phosphate buffered saline (PBS) was immediately applied to the stamp surface and allowed to stand at room temperature. After 30 min, the solution of protein was removed and the inked stamp surface was washed with PBS (2×2 mL), ddH$_2$O (2×2 mL) and, finally, dried under a stream of N$_2$. The stamp was then applied under light pressure to a substrate, previously cleaned by sonication in 2:1 ddH$_2$O/EtOH and dried under a stream of N$_2$, and left in place for several seconds. The stamped substrate was then washed with PBS (2 mL), ddH$_2$O (2 mL) and dried under a stream of N$_2$. A substrate prepared in this manner is shown in FIG. 4, where the deposited material is visualized using atomic force microscopy.

If subsequent patterns were desired on the same substrate, they were produced by using additional PDMS stamps cleaned, inked and stamped in the same manner as above, but cross-stamped onto the substrate at angles offset from the existing patterns.

EXAMPLE 2

Signal Measurement

The substrate was illuminated with either a Nd:YVO$_4$ laser (lambda=532 nm) or a red diode laser (lambda=650 nm). The diffraction image of crossed-stamped substrates resulting from illumination by either laser can be visually observed in transmission or reflection mode prior to addition of analyte. For visual and photographic signal detection, the intensity of the diffracted light was reduced to the point when the diffraction image was no longer discernible by eye using a neutral density filter before the addition of analyte. For electronic signal detection, the intensity was reduced with a neutral density filter to a small, but measurable value to maximize the signal range of the detection device before the addition of analyte.

EXAMPLE 3

"Dry" Measurement

In the "dry" measurement scheme, the substrate was immersed in a solution containing the analyte for the specified period of time. The substrate was then removed from the analyte solution, washed with PBS (2 mL) and ddH$_2$O (2 mL), and dried under a stream of N$_2$. The substrate was illuminated with a laser and a visible diffraction image could be discerned by eye and the intensity measured using a CCD linear array or CCD area array detector hooked up to a computer. Alternatively, a photomultiplier tube mounted on an x-y translation stage was used to measure the signal intensity of a specific spot on the diffraction image by moving it across the spot while recording the intensity on an oscilloscope.

EXAMPLE 4

Goat IgG Patterned Substrate Tested with Anti-goat Gold Conjugates

Figure 3A:
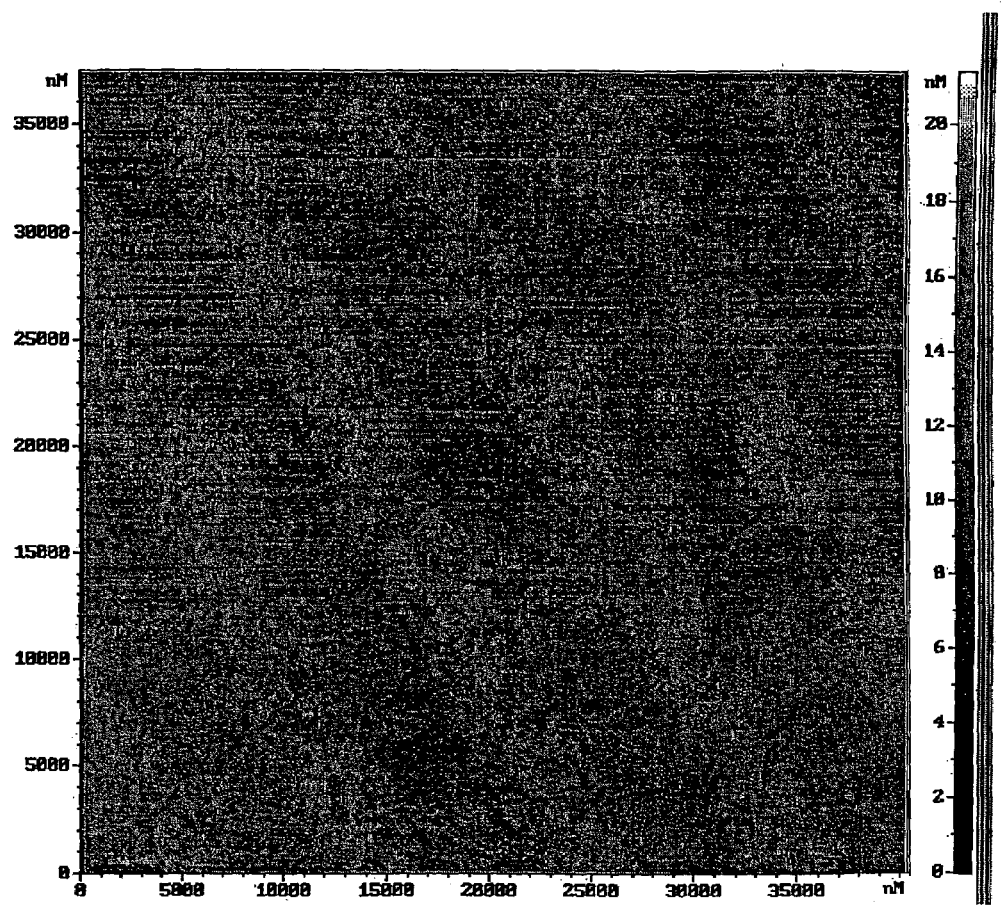
FIG. 3a is a surface prepared with a PRIOR ART pattern of evenly spaced lines of antibody (a 'biograting')
Figure 3B:
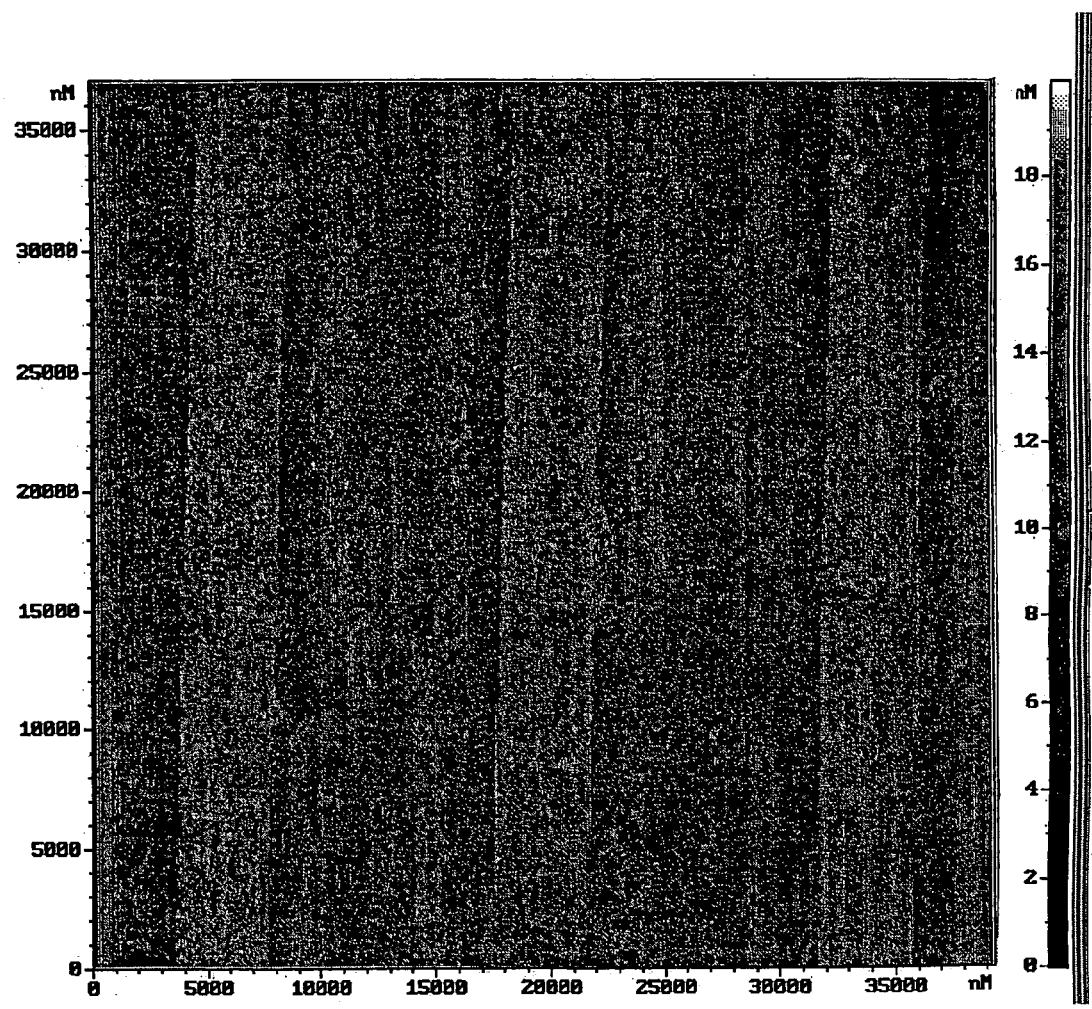
FIG. 3b is a surface prepared with a pattern made using a 6-beam splitter diffractive optic.

Goat IgG was patterned as described above onto two glass substrates using a grating and a six-beam splitter diffractive optic, respectively. FIGS. 3a and 3b are images of these substrates visualized using atomic force microscopy. The resulting patterned substrates were immersed in anti-goat IgG gold conjugate solution for 30-60 min and then removed and washed with PBS (2×2 ml) and ddH$_2$O (2×2 ml) and dried under a stream of N$_2$. The development of the diffraction images observed in both the transmitted and reflected modes corresponding to goat IgG on the substrate was monitored visually and recorded using a CCD camera; image analysis software was utilized to make a comparison of the intensities of the diffracted signal. The results are summarized in FIGS. 4a and 4b. The patterned substrate prepared from a diffractive optic beam splitter as master showed strong diffraction signals away from the centre (main beam), while the substrate prepared using the prior art parallel line grating showed a rapid decay in signal.

As used herein, the terms "comprises", "comprising", "includes" and "including" are to be construed as being inclusive and open ended, and not exclusive. Specifically, when used in this specification including claims, the terms "comprises" and "comprising" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A sensing element for use in a light diffraction assay for detecting the presence or absence of at least one analyte, comprising:

a substrate including a planar surface and analyte-specific recognition binding elements laid out on said planar surface in a pre-selected pattern such that when analytes are present in an assay they bind to said analyte-specific recognition binding elements, said pre-selected pattern being configured so that under illumination by a beam of light a diffraction pattern is produced having at least one diffraction spot spaced from said beam of light and having a sufficient amount of intensity of said diffraction pattern being located at said at least one diffraction spot to indicate presence of analytes bound to said analyte specific recognition binding elements, said pre-selected pattern excluding said analyte-specific recognition binding elements arrayed in parallel straight lines of substantially equal width spaced evenly from each other, or in a periodic array of circles, said pattern of analyte-specific recognition binding elements being a first pattern for binding first analytes present in said medium, and at least a second pattern of analyte-specific recognition binding elements for binding second analytes present in said medium.

2. A sensing element according to claim 1 wherein said pattern of analyte-specific recognition binding elements is applied to said planar surface by stamping using a stamp coated with said analyte-specific recognition binding elements.

3. A sensing element according to claim 2 wherein said stamp is made using a diffractive optic element having a surface relief pattern as a master.

4. The sensing element according to claim 1 wherein said substrate is substantially transparent and when said surface is illuminated from one side of said substrate light diffracted from said substrate is detected on the opposite side of said substrate.

5. A sensing element for use in a light diffraction assay for detecting the presence or absence of at least one analyte, comprising:

a substrate having analyte-specific receptors bound to a surface of said substrate for binding selected analytes, said surface of said substrate having a surface topography configured such that, upon illumination by a beam of light and with analytes bound to said analyte-specific receptors, gives rise to a sufficient number of diffraction spots in pre-selected positions spaced from said beam of light indicative of the presence of analytes bound to said analyte-specific receptors, and wherein said surface topography is defined by a sinusoidal surface pattern extending across said surface.

6. The sensing element according to claim 5 wherein said sinusoidal surface pattern has a periodicity in a range from about half to about ten times the wavelength of the light beam, and wherein said pre-selected number of diffraction spots is one diffraction spot.

7. A sensing element for use in a light diffraction assay for detecting the presence or absence of at least one analyte, comprising:
a substrate having analyte-specific receptors bound to a surface of said substrate for binding selected analytes said surface of said substrate having a surface topography configured such that, upon illumination by a beam of light and with analytes bound to said analyte-specific receptors, gives rise to a sufficient number of diffraction spots in pre-selected positions spaced from said beam of light indicative of the presence of analytes bound to said analyte-specific receptors, wherein said surface topography includes submicroscopic sized indentations in the surface substrate that provide a complementary geometry to said analytes so that said indentations are the analyte specific receptors.

8. A sensing element for use in a diffraction binding assay method for detecting analytes comprising:
a substrate having analyte-specific receptors bound to a surface of said substrate for binding selected analytes, said surface of said substrate having a surface topography configured such that, upon illumination by a beam of light and with analytes bound to said analyte-specific receptors, gives rise to a sufficient number of diffraction spots in pre-selected positions spaced from said beam of light indicative of the presence of analytes bound to said analyte-specific receptors,
wherein the presence of analytes in a medium are tested for by
contacting said surface of the substrate with a medium being tested for presence or absence of said analytes for a sufficient time to permit preselected analytes present in solution to bind with their analyte-specific receptors, and
illuminating said substrate with a beam of light and detecting light diffracted from said substrate surface and analysing said diffracted light for presence of diffraction spots representative of binding of said analyte to said analyte-specific receptors on said surface and
wherein said surface topography is defined by a sinusoidal surface pattern extending across said surface.

9. The sensing element for use in the diffraction binding assay method for detecting analytes according to claim 8 wherein said medium is a solution having a refractive index closely matched to a refractive index of said substrate, and wherein said substrate is immersed in said solution such that an interface between said substrate surface and said solution is substantially invisible so that little or no light is diffracted prior to binding of the analytes to the analyte-specific receptors, and wherein binding of the analytes to the analyte-specific receptors reduces the refractive index matching between solution and substrate to give rise to said diffraction spots.

10. The sensing element for use in the diffraction binding assay method for detecting analytes according to claim 8 wherein said sinusoidal surface pattern has a periodicity in a range from about half to about ten times a wavelength of the beam of light, and wherein said pre-selected number of diffraction spots is one diffraction spot.

11. The sensing element for use in the diffraction binding assay method for detecting analytes according to claim 8 wherein said substrate is substantially transparent and when said surface is illuminated from one side of said substrate light diffracted from said substrate is detected on the opposite side of said substrate.

12. The sensing element for use in the diffraction binding assay method for detecting analytes according to claim 8 wherein said substrate is partially reflecting and when said surface is illuminated from one side thereof diffracted light is detected on the same side of said substrate.

13. The sensing element for use in the diffraction binding assay method for detecting analytes according to claim 8 wherein said substrate is reflecting, and when said surface is illuminated from one side thereof diffracted light is detected on the same side of said substrate.

14. The sensing element for use in the diffraction binding assay method for detecting analytes according to claim 8 including detecting light diffracted from said substrate surface prior to exposure of said substrate surface to said medium for producing a baseline diffraction image due to said substrate and analyte-specific receptor patterns in the absence of analytes, including storing said baseline diffraction image.

15. The sensing element for use in the diffraction binding assay method for detecting analytes according to claim 14 wherein analysing said diffracted light for the presence of a diffraction spots representative of binding analyte with its analyte-specific receptor includes comparing said diffraction image with said baseline diffraction image.

16. The sensing element for use in the diffraction binding assay method for detecting analytes according to claim 8 wherein said beam of light is a substantially coherent, monochromatic laser beam.

17. The sensing element for use in the diffraction binding assay method for detecting analytes according to claim 16 wherein said laser beam has a wavelength in the infrared, visible or ultraviolet spectral region.

18. A sensing element for use in a light diffraction assay for detecting the presence or absence of at least one analyte, comprising:
a substrate including a planar surface and analyte-specific recognition binding elements laid out on said planar surface in a pre-selected pattern such that when analytes are present in an assay they bind to said analyte-specific recognition elements, said pre-selected pattern being configured so that illumination of said pre-selected pattern by a beam of light and with analytes bound to said analyte-specific recognition binding elements gives rise to a sufficient number of diffraction spots in pre-selected positions spaced from said beam of light indicative of the presence of analytes bound to said analyte-specific recognition binding elements, and wherein said pattern of analyte-specific recognition binding elements is a first pattern for binding first analytes present in said medium, including at least a second pattern of analyte-specific recognition binding elements for binding at least second analytes present in said medium.

19. A sensing element for use in a light diffraction assay for detecting the presence or absence of at least one analyte, comprising:
a substrate including a planar surface and analyte-specific recognition binding elements laid out on said planar surface in a pre-selected pattern such that when analytes are present in an assay they bind to said analyte-specific recognition binding elements, said pre-selected pattern being configured so that under illumination by a beam of light a diffraction pattern is produced having at least one diffraction spot spaced from said beam of light and having a sufficient amount of intensity of said diffraction pattern being located at said at least one diffraction spot to indicate presence of analytes bound to said analyte specific recognition binding elements, said pre-selected pattern excluding said analyte-specific recognition binding elements arrayed in parallel straight lines of substantially equal width spaced evenly from each other, or in a periodic array of circles, wherein said substrate is partially reflecting and when said surface is illuminated from one side thereof diffracted light is detected on the same side of said substrate.

20. A sensing element according to claim 19 wherein said pattern of analyte-specific recognition binding elements is applied to said planar surface by stamping using a stamp coated with said analyte-specific recognition binding elements.

21. A sensing element according to claim 20 wherein said stamp is made using a diffractive optic element having a surface relief pattern as a master.

22. A sensing element for use in a light diffraction assay for detecting the presence or absence of at least one analyte, comprising:

a substrate including a planar surface and analyte-specific recognition binding elements laid out on said planar surface in a pre-selected pattern such that when analytes are present in an assay they bind to said analyte-specific recognition binding elements, said pre-selected pattern being configured so that under illumination by a beam of light a diffraction pattern is produced having at least one diffraction spot spaced from said beam of light and having a sufficient amount of intensity of said diffraction pattern being located at said at least one diffraction spot to indicate presence of analytes bound to said analyte specific recognition binding elements, said pre-selected pattern excluding said analyte-specific recognition binding elements arrayed in parallel straight lines of substantially equal width spaced evenly from each other, or in a periodic array of circles, wherein said substrate is reflecting, and when said surface is illuminated from one side thereof diffracted light is detected on the same side of said substrate.

23. A sensing element according to claim 22 wherein said pattern of analyte-specific recognition binding elements is applied to said planar surface by stamping using a stamp coated with said analyte-specific recognition binding elements.

24. A sensing element according to claim 23 wherein said stamp is made using a diffractive optic element having a surface relief pattern as a master.

25. A sensing element for use in a light diffraction assay for detecting the presence or absence of at least one analyte, comprising:

a substrate including a planar surface and analyte-specific recognition binding elements laid out on said planar surface in a pre-selected pattern such that when analytes are present in an assay they bind to said analyte-specific recognition binding elements, said pre-selected pattern being configured so that under illumination by a beam of light a diffraction pattern is produced having at least one diffraction spot spaced from said beam of light and having a sufficient amount of intensity of said diffraction pattern being located at said at least one diffraction spot to indicate presence of analytes bound to said analyte specific recognition binding elements, said pre-selected pattern excluding said analyte-specific recognition binding elements arrayed in parallel straight lines of substantially equal width spaced evenly from each other, or in a periodic array of circles.

26. A sensing element according to claim 25 wherein said pattern of analyte-specific recognition binding elements is applied to said planar surface by stamping using a stamp coated with said analyte-specific recognition binding elements.

27. A sensing element according to claim 25 wherein said stamp is made using a diffractive optic element having a surface relief pattern as a master.

* * * * *